United States Patent
Bock et al.

(10) Patent No.: US 6,393,319 B1
(45) Date of Patent: May 21, 2002

(54) METHODS AND APPARATUS FOR PORTABLE DELIVERY OF ELECTRICAL PHYSICAL MODALITIES TO A PATIENT

(75) Inventors: Christopher Bock, 3435 NE. Clackamas St., Portland, OR (US) 97232; Steven Geist, Portland, OR (US)

(73) Assignee: Christopher Bock, Portland, OR (US)

( * ) Notice: Subject to any disclaimer, the term of this patent is extended or adjusted under 35 U.S.C. 154(b) by 0 days.

(21) Appl. No.: 09/423,479
(22) PCT Filed: May 6, 1998
(86) PCT No.: PCT/US98/09304
§ 371 Date: Nov. 5, 1999
§ 102(e) Date: Nov. 5, 1999
(87) PCT Pub. No.: WO98/50107
PCT Pub. Date: Nov. 12, 1998

Related U.S. Application Data

(60) Provisional application No. 60/045,775, filed on May 6, 1997.

(51) Int. Cl.⁷ .................................................. A61N 1/00
(52) U.S. Cl. ............................ 607/2; 607/76; 607/46
(58) Field of Search ........................... 600/26, 27, 28; 607/2, 3, 45, 46, 48, 50, 62, 67, 69, 72, 75, 76

(56) References Cited

U.S. PATENT DOCUMENTS

| | | | |
|---|---|---|---|
| 4,875,484 A | * 10/1989 | Anzai et al. | 128/421 |
| 5,441,528 A | * 8/1995 | Chang et al. | 607/69 |
| 5,562,717 A | 10/1996 | Tippey et al. | |
| 5,616,140 A | 4/1997 | Prescott | |
| 5,679,004 A | * 10/1997 | McGowan et al. | 434/247 |
| 5,702,428 A | * 12/1997 | Tippey et al. | 607/41 |
| 5,725,563 A | * 3/1998 | Klotz | 607/62 |

* cited by examiner

Primary Examiner—Jeff Jastrab
Assistant Examiner—Frances P. Oropeza
(74) Attorney, Agent, or Firm—Marger Johnson & McCollom, PC

(57) ABSTRACT

Data defining electrical waveforms for physical therapy is created on a computer and stored in a removable machine-readable medium such as a CD-ROM or semiconductor memory module. The data is played back, for example on a portable CD-ROM player, to produce the physical therapy waveforms at any time and location convenient or desired by the patient. An interface circuit amplifies and conditions the resulting waveforms for applying them to the skin of the patient via leads and electrodes. Since most therapies use waveforms within the audio frequency range, ubiquitous low-cost audio playback equipment can be used. Advantages of the invention are providing physical therapy at any location and at low cost, without requiring presence of a clinician or other health care professional on location.

32 Claims, 3 Drawing Sheets

METHODS AND APPARATUS FOR PORTABLE DELIVERY OF ELECTRICAL PHYSICAL MODALITIES TO A PATIENT

This Appln. is a 371 of PCT/US 98/09304 filed May 6, 1998 which claims benefit of Prov. No. 60/045,775 filed May 6, 1997.

BACKGROUND OF THE INVENTION

The general subject matter is methods and apparatus for use in physical therapy to alleviate pain, improve mobility, etc., for a human patient who suffers from a disease or injury treatable by physical therapy. Various physical therapy machines are known in the prior art. Specifically, the present invention is related to machines that apply electrical energy to the affected part of the body. It has been found that the application of electrical energy at particular amplitudes and frequencies can be a helpful physical therapy modality. It also appears that many of these treatment modalities apply electrical energy that oscillates at frequencies in the audio range, i.e., from about 20 Hz to about 20,000 Hz. In general, a physical therapy machine is set to provide particular electrical signals, an these are applied to the body through electrodes or "pads" which are applied to the skin in various locations. Known physical therapy machines are bulky, expensive and require training and expertise to operate. For these reasons, their use is generally limited to the doctor's office or physical therapy clinic.

SUMMARY OF THE INVENTION

The present invention does not provide new physical therapy modalities. Rather, it is directed to new ways to specify (prescribe) appropriate modalities for a patient, and new ways to deliver therapy, i.e. electrical energy to the patient's body in accordance with the prescribed modalities. As illustrated in the enclosed drawings, the clinician has access to a computer (PC) of the type that are in common use today, including a CD ROM drive and a "sound card." Sound cards are known in the prior art for generating audio output, e.g., music, to internal or external speakers of headphones. According to one aspect of the present invention, the appropriate waveforms, amplitudes and frequencies, are specified in the personal computer and generated by the sound card in response to those specifications. However, rather than output these audio signals through speakers or headphones, the output from the sound card is directed through a novel "interface" via wires to electrode or pads which are applied to the patient's body for deliver of a corresponding electrical stimuli. The interface contains suitable electronics for transmitting these signals to the electrodes, and for limiting the signals so as to prevent voltage or energy levels that would be unsafe.

Accordingly, one aspect of the invention is an apparatus for administering electrical physical therapy to a patient. The apparatus includes: a playback device for reading prerecorded information defining at least one electrical waveform and reproducing the waveform; an interface circuit for amplifying the resulting waveform so as to form one or more output signals; at least two electrodes for applying the output signal to the skin of the patient; and a lead for interconnecting each of the electrodes to the interface circuit to convey the corresponding output signal to a respective one of the electrodes. In one example, the playback device can be a computer with a CD-ROM drive, or a portable CD-ROM player. Solid-state or semiconductor memory can be used to record the therapy data as well. The prerecorded information can include two interferential audio frequency analog signals stored on a the machine-readable medium.

The inventive system can be used at home, or anywhere a personal computer can be found, as long as the patient has the appropriate interface and pads. Thus, for example, the treatment is designed and specified by the clinician, and recorded on a machine-readable medium such as a floppy disk, tape or CD. The patient takes the "digital prescription" with him, along with the interface and leads, and by "playing" the prescribed therapies through his own personal computer, can received prescribed physical therapy treatment as and where needed.

Another aspect of the invention thus can be described as a method of prescribing and delivering electrical physical therapy to the body of a patient, the method comprising the steps of:

selecting a physical therapy treatment modality in terms of one or more electrical waveforms having selected amplitudes and frequencies;

recording the said waveforms on a machine-readable recording medium;

delivering the recording medium to the patient;

reading the waveforms from the recording medium using an audio playback device to form audio frequency signals;

converting the audio frequency signals to physical therapy electrical signals; and applying the physical therapy electrical signals to the body of the patient to deliver the selected physical therapy treatment modality to the patient.

These and other features and advantages are more fully described below with reference to the appended drawings.

DETAILED DESCRIPTION OF A PRESENTLY PREFERRED EMBODIMENT

Figure 1:
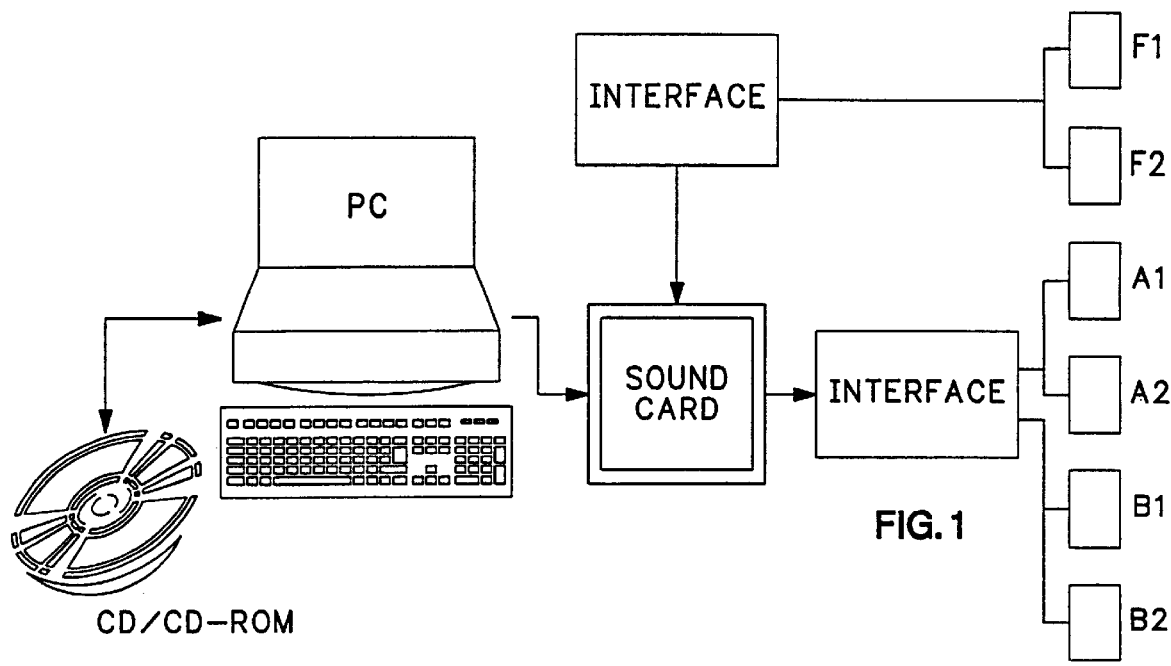
FIG. 1 is a simplified block diagram of a system for prescribing and administering an electrical physical therapy treatment to a patient according to the present invention.

FIG. 1 shows a system for creating or "prescribing" an electrical physical therapy treatment and treating a patient. A clinician uses the computer ("PC") to define one or more waveforms for electrical physical therapy. Data defining the waveforms is stored in machine-readable form, e.g. on a CD (compact disc). The audio "sound card" in the computer is used to generate audio frequency signals responsive to the stored data. The audio signals are output to an interface circuit further described below, which in turn provides output signals to patient electrodes or "pads" A1,A2 and B1,B2. A single pair of pads can be used for a single-channel modality, while two pairs of pads as illustrated are used for interferential treatment modalities further described later.

Biofeedback pads F1,F2 can be used to provide biofeedback to the computer during therapy. This data can be stored and synchronized to the treatment data for examination by the clinician, either real-time for tailoring the treatment, or later. A biofeedback interface circuit amplifies the biofeedback signals and converts them to audio form for convenient input to the computer via the sound card microphone input jack.

Figure 2:
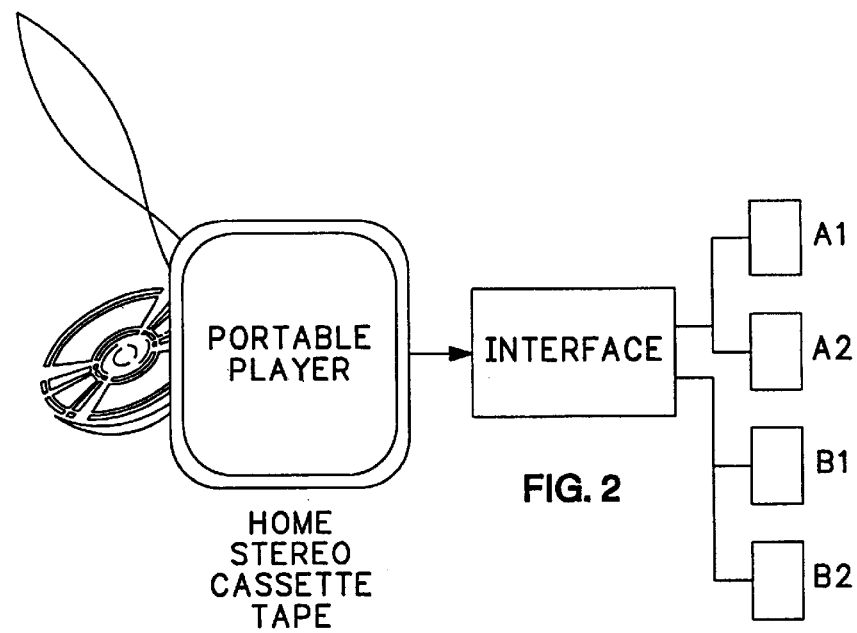
FIG. 2 is a simplified block diagram of a portable playback system for administering electrical physical therapy to a patient at any convenient location.

FIG. 2 shows a playback device, e.g. a portable CD player, and interface circuit connected to the audio output (headphone) jack of the playback device. Leads and electrodes are connected to the interface circuit as in FIG. 1 for applying the prescribed therapy to the patient. Other playback devices, e.g. home stereo, cassette tape, etc. can be used in like manner. Digital data storage is preferred for its reliability and accuracy, but other methods, e.g. magnetic tape can be used. In general, all the patient requires is a CD or other memory module with the prescribed therapy recorded on it, the playback device, interface and leads. Various treatment modes can be recorded on different portions of the memory. The prescribed therapy can be used anytime and anywhere desired by the patient.

Another important feature of the inventive system, as mentioned, is the use of biofeedback. Additional leads can be applied to the patient's body (see FIG. 1) to provide real-time biofeedback during treatment. For example, if the clinician is supervising the therapy using a personal computer, the same personal computer can receive and record biofeedback data during the treatment, so that the clinician can observe the effectiveness or response to the treatment. This data can be recorded for review at a convenient time and place. Thus, for example, the patient could received the treatments at home, as described above, using his personal computer. At the same time, the patient could apply the additional leads and inputs into the computer to collect biofeedback data. Then the patient could provide that data stored in a digital machine-readable format, back to the clinician for review and evaluation.

It can be appreciated that the use of the personal computer, and well-known consumer audio equipment for physical therapy according to the invention, can result in dramatic reduction of costs of physical therapy equipment, and other benefits as mentioned. The invention is not limited to audio frequencies, however. The same concept can be used to store (record) waveform data outside the audible range. For example, present CD technology provides for recording down in the 1 Hz range. The invention can be used for low-frequency therapies as well.

Figure 3:
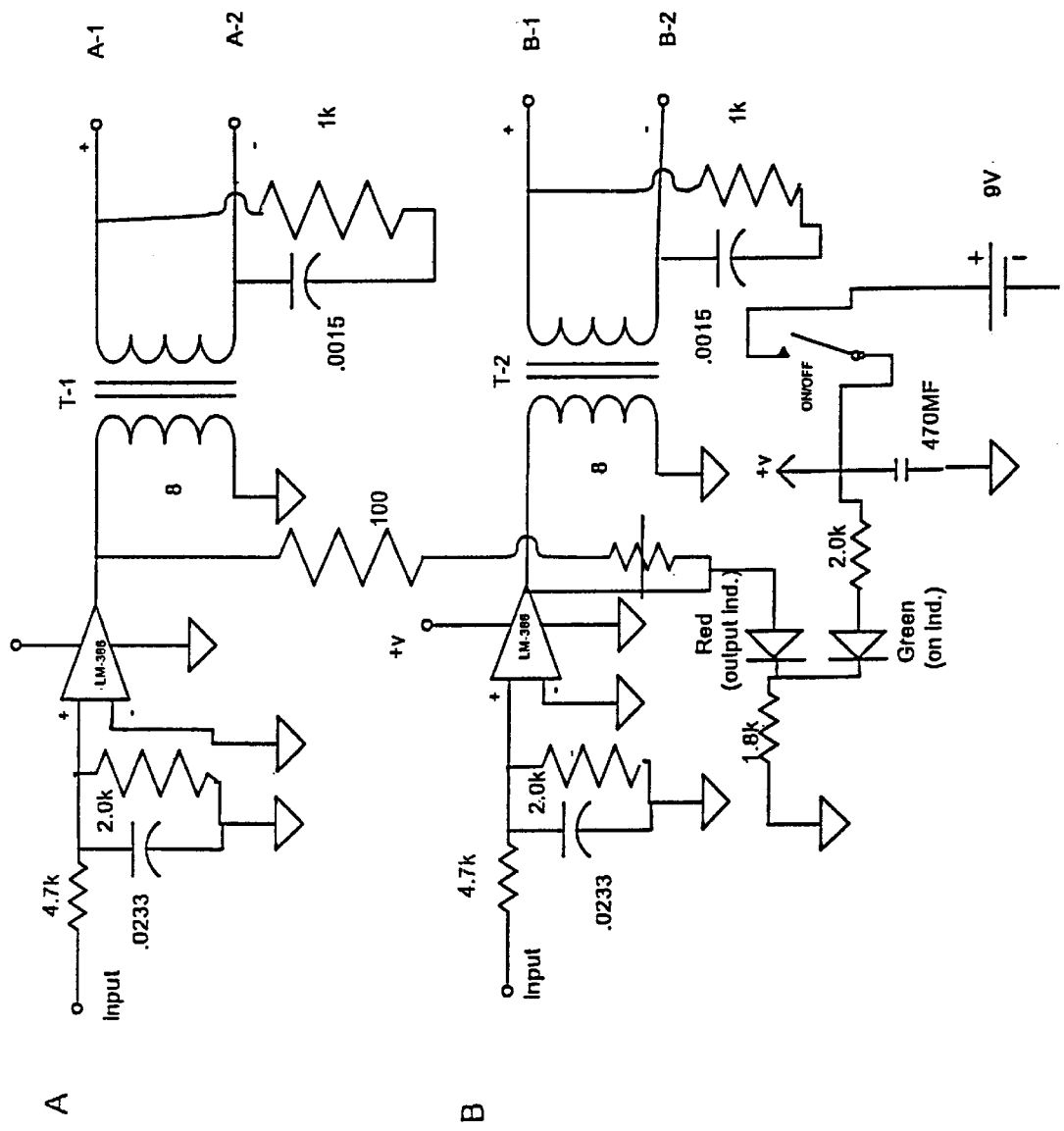
FIG. 3 is a schematic diagram of an illustrative interface circuit for interfacing an electrical signal to a plurality of patient electrodes to administer electrical physical therapy.

FIG. 3 is an electronic schematic diagram of a representative embodiment of the interface apparatus. Its function is to convert the voltages and currents from an audio or digital source into a form appropriate for physical therapy, such as interferential stimulation, and to provide isolation between the input and output sources. In the figure, a monolithic amplifier LM-386, or a similar device, is arranged to provide signal voltage and current gain for proper level conversion. The transformers, T-1 and T-2, have an output radio of approximately 1:8. The transformer steps up the output voltage from the monolithic amplifier from approximately 7 volts to 60 volts, for example, at the transformer output. Other voltage levels can be used, and the output voltage range can be made adjustable.

The transformers also provide isolation between the input and output of the interface for safety. The transformers are selected to saturate the cores at modest current levels, for example no more than 10 mA, again for safety, so that no more than 10 mA of current can be delivered to the patient. The operating frequency of the interface circuitry preferably includes a range of at least 20 Hz to 20 kHz, although a broader range—beyond audio—can be useful as well. The outputs, A-1, A-2 and B-1, B-2 are connected via wire leads to standard electrodes or "pads" which are adhered to a patient's skin, or held in place by a strap, elastic bandage or the like to apply the output energy from the interface to the patient. The particulars of electrodes for connection to the human body are well known and widely available commercially. The particular electronic circuit illustrated in the figure, and the specific component values shown in the schematic, are merely illustrative rather than limiting. Similar functionality could be achieved by various electrical circuits, using discrete and/or semiconductor integrated circuit components. All of the components shown in the illustrative embodiment are widely available at modest cost.

In the arrangement illustrated, a two-channel (stereo) signal is input to the interface circuit from an audio source. Two channels or signals can conveniently be recorded to provide interferential therapy modalities. Such modalities typically provide a constant frequency signal on one channel, and a varying frequency signal on the other channel. Variations in the frequency of the second channel modulate a difference between the two channels; and that difference appears (amplified) across the corresponding pair of electrodes. For example, in FIG. 3, the input signal at A may have a constant frequency, while the input signal at B may vary over time. The four outputs will provide the interferential therapy to the patient. The wave-shapes (triangle, squarewave, sine, etc.), amplitudes and frequencies are selected by the doctor or clinician who prescribes the therapy. The clinician also specifies the rate of change of the second channel in the case of interferential therapy. For example, the second channel frequency might be varied over a range of +/−200 Hz relative to the first channel (fixed) frequency. The variation in frequency might occur over a few seconds or even minutes; it can be regular (periodic) or random. Virtually any waveforms can be recorded and played back to provide therapy using the methods and apparatus of the present invention.

Figure 4:
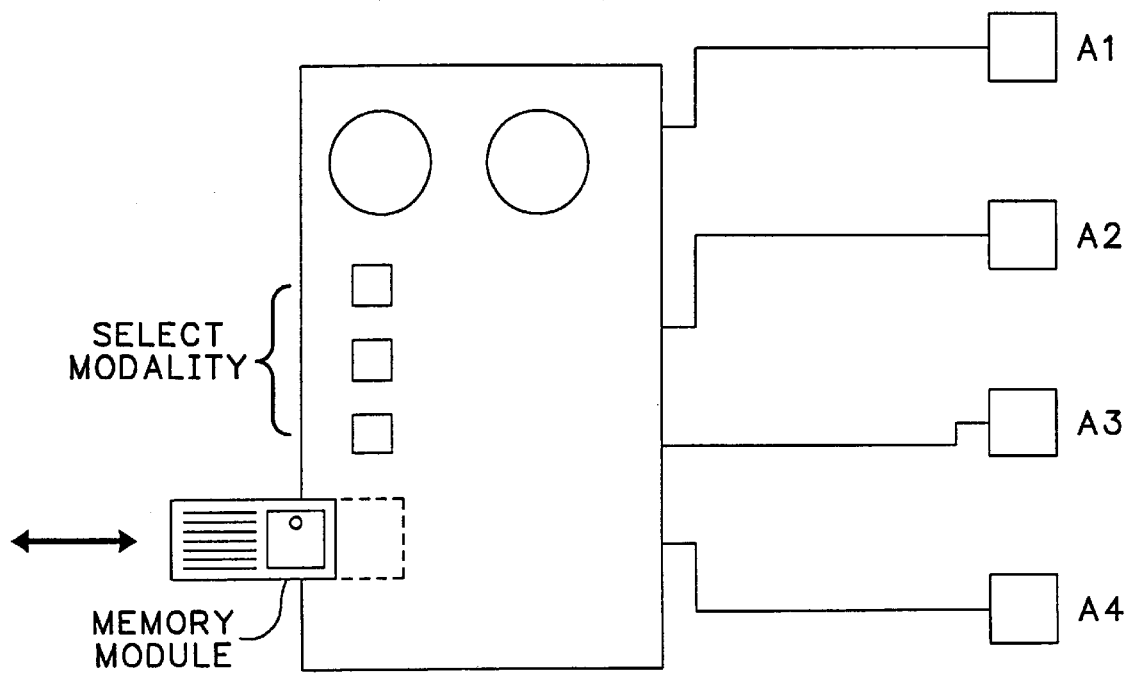
FIG. 4 is an illustration of an alternative portable playback system having a removable memory module for administering electrical physical therapy to a patient according to data stored in the removable memory module.

FIG. 4 illustrates an alternative embodiment of the invention. Here, a portable device receives a removable memory module on which the therapy waveforms (or data defining such waveforms) is stored. The memory module can comprise semiconductor (solid-state) memory, e.g. non-volatile RAM, ROM, FLASH etc. or it can comprise a rotating magnetic media (hard disk) in a PCM type of form factor. Any digital data storage medium can be used for the present purposes. It will provide for the patient to receive a physical therapy "prescription" in the form of digital data; and allow the patient to receive the corresponding treatment anytime and anywhere using the playback device. The device in FIG. 4 includes electronic circuitry for reading the stored digital data from the removable module; converting that data to waveforms of specified frequency, voltage, etc. characteristics; and outputting the waveforms to the electrodes for treating the patient. A battery—preferably rechargeable—can be used as a portable power supply. Buttons on the device can be used to select one of several treatment modalities stored on the memory module. A new "digital prescription" can be delivered to the patient simply by sending the patient a new memory module containing the new data; or by downloading the new data via telecom or internet. Accordingly, much time and money is saved over prior art arrangements which require patient attendance at a clinic to receive electrical physical therapy.

What is claimed is:

1. Apparatus for administering electrical physical therapy to a patient, comprising:
    an audio playback device adapted to play prerecorded audio signals;
    an interface circuit connectable to receive and amplify the audio signals;
    at least two electrodes adapted to directly apply the amplified audio signals to skin of the patient; and
    a lead for interconnecting each of the at least two electrodes to the interface circuit to convey a corresponding amplified audio signal to a respective of one of the electrodes.

2. Apparatus according to claim 1 wherein the prerecorded audio signals comprises at least two interferential audio frequency analog signals stored on a machine-readable medium.

3. Apparatus according to claim 2 wherein the machine-readable medium consists of magnetic tape.

4. Apparatus according to claim 1 wherein the prerecorded audio signals comprises digital data defining one or more audio frequency analog signals, stored on a machine-readable medium.

5. Apparatus according to claim 4 wherein the machine-readable medium consists of random access memory.

6. Apparatus according to claim 4 wherein the machine-readable medium consists of a CD-ROM.

7. Apparatus according to claim 4 wherein the machine-readable medium consists of semiconductor memory.

8. Apparatus according to claim 4 wherein the machine-readable medium consists of a PCM-CIA card memory.

9. Apparatus according to claim 1 wherein the audio playback device comprises a portable audio playback device.

10. Apparatus according to claim 9 wherein the audio playback device comprises a portable CD-ROM player.

11. Apparatus according to claim 9 wherein the audio playback device comprises a computer.

12. Apparatus according to any of claims 1-8 wherein the interface circuit includes an input jack connectable to an audio output jack of the audio playback device to receive the audio signals.

13. Apparatus according to claim 1 wherein the prerecorded audio signals comprise digital data defining one or more audio frequency analog signals, stored on a machine-readable medium, and the analog signals form a selected physical therapy modality.

14. Apparatus according to claim 13 wherein the selected physical therapy modality comprises at least one of interferential, low and/or high voltage galvanic, muscle stimulation, micro-current, Russian stimulation, transcutaneous electrical nerve stimulation (T.E.N.S.), Faradic, and synaptic electronic activation therapy modalities.

15. Apparatus according to claim 1 wherein the prerecorded audio signals comprise digital data defining two or more physical therapy modalities, the data defining each modality stored on a respective track of a machine-readable medium, thereby allowing the patient to receive a selected one of the physical therapy modalities by playing the corresponding track on the audio playback device.

16. A system for prescribing an electrical physical therapy treatment, comprising:
    a computer having a display and input means for receiving input from a user to allow the user to define a physical therapy treatment; and
    storage means connected to the computer for storing audio signals representing the defined physical therapy treatment onto a removable, machine-readable media, thereby allowing delivery of the defined physical therapy treatment directly to a patient in a convenient, portable form by delivering the removable media to the patient.

17. A system according to claim 16 wherein the audio signals representing the defined physical therapy treatment comprises at least one audio frequency waveform.

18. A system according to claim 16 wherein the audio signals representing the defined physical therapy treatment comprises digital data representing at least one audio frequency waveform.

19. A system according to claim 16 wherein the audio signals representing the defined physical therapy treatment comprises digital data representing an interferential pair of audio frequency waveforms.

20. A system according to claim 17 wherein the input means for receiving input from a user allows the user to select a frequency and an amplitude of said at least one audio frequency waveform.

21. A system according to claim 16 wherein the storage means includes means for storing the data onto a writable CD-ROM.

22. A system according to claim 16 wherein the storage means includes means for storing the data into a semiconductor memory.

23. A system according to claim 16 wherein the storage means includes means for storing the data onto a magnetic recording tape.

24. A system according to claim 16 wherein the storage means includes means for downloading the data from a remote location.

25. A method of prescribing and delivering electrical physical therapy to the body of a patient, comprising:
    selecting a physical therapy treatment modality in terms of one or more audio frequency waveforms having selected amplitudes and frequencies;
    recording the audio frequency waveforms on a machine-readable recording medium;
    reading the audio frequency waveforms from the recording medium using an audio playback device to form audio frequency signals;
    amplifying the audio frequency signals; and
    applying the amplified audio frequency signals directly to the body of the patient thereby delivering the selected physical therapy treatment modality to the patient.

26. A method according to claim 25 wherein the recording comprises recording the audio frequency waveforms as digital data.

27. A method according to claim 26 wherein said recording medium consists of semiconductor memory.

28. A method according to claim 26 wherein said recording medium consists of a CD-ROM.

29. A method according to claim 26 wherein the amplifying includes increasing a voltage of the audio frequency signals.

30. A method according to claim 26 wherein the amplifying includes isolating the audio frequency signals from the amplified audio frequency patient.

31. A method according to claim 26 wherein the amplifying includes limiting a voltage of the amplified audio frequency signals.

32. Apparatus according to claim 1 wherein the prerecorded audio signals are downloadable via an internet connection.

* * * * *

UNITED STATES PATENT AND TRADEMARK OFFICE
CERTIFICATE OF CORRECTION

PATENT NO. : 6,393,319 B1
DATED : May 21, 2002
INVENTOR(S) : Christopher Bock

It is certified that error appears in the above-identified patent and that said Letters Patent is hereby corrected as shown below:

Column 1,
Line 23, "an these" should be -- and these --.
Line 41, "of headphones" should be -- or headphones --.
Line 50, "deliver" should be -- delivery --.

Column 2,
Line 2, "on a the" should be -- on a --.
Line 11, "can received" should be -- can receive --.
Line 33, "received" should be -- receive --.

Column 3,
Line 58, "radio" should be -- ratio --.

Column 5,
Line 4, "an audio playback" should be -- a playback --.
Line 11, "a corresponding" should be -- the corresponding --.

Column 6,
Line 30, "from a remote location" should be -- from an internet location --.
Line 59, "from the amplified" should be --from the physical --.
Line 60, "amplifying" should be -- converting --.

Signed and Sealed this

Tenth Day of December, 2002

JAMES E. ROGAN
*Director of the United States Patent and Trademark Office*